(12) United States Patent
Jeong et al.

(10) Patent No.: US 7,952,959 B2
(45) Date of Patent: May 31, 2011

(54) PHANTOM FOR STANDARDIZING ULTRASONOGRAPH AND METHOD OF OBTAINING STANDARDIZED ULTRASONOGRAPHIC IMAGE USING THE PHANTOM

(75) Inventors: Ji Wook Jeong, Daejeon (KR); Sooyeul Lee, Daejeon (KR); Jeong Won Lee, Daejeon (KR); Done Sik Yoo, Daejeon (KR); Seunghwan Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 854 days.

(21) Appl. No.: 11/877,883

(22) Filed: Oct. 24, 2007

(65) Prior Publication Data

US 2008/0139933 A1   Jun. 12, 2008

(30) Foreign Application Priority Data

Dec. 6, 2006   (KR) .................. 10-2006-0123399
Feb. 27, 2007   (KR) .................. 10-2007-0019903

(51) Int. Cl.
*A61B 8/00*   (2006.01)
(52) U.S. Cl. ........................................... 367/13
(58) Field of Classification Search .................... 367/13, 367/11, 7; 73/1.86, 1.82, 600; 600/437, 600/459, 472
See application file for complete search history.

(56) References Cited

U.S. PATENT DOCUMENTS

| | | | |
|---|---|---|---|
| 4,277,367 A * | 7/1981 | Madsen et al. ................. | 73/600 |
| 5,944,665 A | 8/1999 | Iino et al. | |
| 6,656,121 B2 | 12/2003 | Jeong et al. | |
| 2003/0122544 A1 * | 7/2003 | Parker et al. .................. | 324/309 |
| 2005/0227364 A1 | 10/2005 | Madsen et al. | |
| 2008/0139933 A1 * | 6/2008 | Jeong et al. .................. | 600/437 |

FOREIGN PATENT DOCUMENTS

| | | |
|---|---|---|
| JP | 2006-166956 | 6/2006 |
| KR | 1999-0063708 | 7/1999 |
| KR | 1020030065155 A | 6/2003 |
| KR | 10-2004-0095467 | 11/2004 |

OTHER PUBLICATIONS

Goodsitt et al.; Real-time B-mode ultrasound quality control test procedures a) Report of AAPM Ultrasound Task Group No. 1 (Aug. 1998) pp. 1385-1406.*
English-language Abstract of WIPO patent document No. WO98/05258.

\* cited by examiner

*Primary Examiner* — Dan Pihulic
(74) *Attorney, Agent, or Firm* — Rabin & Berdo, P.C.

(57) ABSTRACT

Provided are a phantom for standardizing ultrasonograph and a method of obtaining an ultrasonographic image using the phantom, and more particularly, a phantom for measuring fat content in a target organ as a gray level distribution using an ultrasonographic image and assessing the accuracy of ultrasonograph and a method and apparatus for obtaining a standardized ultrasonographic image using the phantom. Since the photographing characteristics of the ultrasonograph are readjusted using a phantom which comprises a phantom part including a strong ultrasonic echo material and a weak ultrasonic echo material, which create a gray level distribution in ultrasonography, in a specific composition and ratio, and assesses the accuracy of the ultrasonograph by comparing the composition and ratio of the materials with a composition and ratio of a gray level in an ultrasonographic image, the characteristics of the ultrasonograph can be standardized and fat content in a body part can be quantitatively measured without being affected by photographing techniques and conditions.

19 Claims, 3 Drawing Sheets

PHANTOM FOR STANDARDIZING ULTRASONOGRAPH AND METHOD OF OBTAINING STANDARDIZED ULTRASONOGRAPHIC IMAGE USING THE PHANTOM

CROSS-REFERENCE TO RELATED PATENT APPLICATION

This application claims the benefit of Korean Patent Application No. 10-2006-0123399, filed on Dec. 6, 2006 and Korean Patent Application No. 10-2007-0019903, filed on Feb. 27, 2007 in the Korean Intellectual Property Office, the disclosures of which are incorporated herein in their entirety by reference.

BACKGROUND OF THE INVENTION

1. Field of the Invention

The present invention relates to a phantom for standardizing ultrasonograph and a method of obtaining an ultrasonographic image using the phantom, and more particularly, to a phantom for measuring fat content in a target organ as a gray level distribution using an ultrasonographic image and assessing the accuracy of ultrasonograph and a method and apparatus for obtaining a standardized ultrasonographic image using the phantom.

The present invention was supported by the Information Technology (IT) Research & Development (R&D) program of the Ministry of Information and Communication (MIC) [Project management number: 2005-S-069-02, Project title: Development of Wearable System Using Physiological Signal Processing].

2. Description of the Related Art

Ultrasonic waves are sound waves having frequencies above the limits of human audibility. Since ultrasonic waves have short wavelengths and high directivity, ultrasonic waves can be used as a fish finder or a sonar that sends out an acoustic pulse in water and measure distances. Ultrasonic waves can also be used to detect flaws in a solid material, cut or process jewelry or glass, and produce, clean, and sterilize emulsion.

Above all, ultrasonic waves can be used to detect abnormalities on human or animal tissues, and ultrasonic diagnostic systems for such diagnostic purposes are widely used. The ultrasonic diagnostic systems can also detect abnormalities in human or animal bodies in a non-invasive manner. Accordingly, the debate over the use of the ultrasonic diagnostic systems to diagnose many current diseases, e.g., obesity, which is defined as an excessively high amount of body fat and may cause other diseases, is now active. Particularly, the use of the ultrasonic diagnostic systems to measure fat content in a human organ, which is difficult to assess visually, is actively being debated.

Deposits of fat in a human organ may develop various complications, and itself may cause malfunction of the human organ. For example, a fatty liver containing abnormally much fat does not cause pain and does not produce any specific symptoms. Although a slight fatty liver can be found in a healthy person, there is a high probability that fat content in the liver increases abnormally and causes a complication or a hepatocirrhosis. As diet life and obesity are becoming social issues, much attention is drawn to the assessment of fat content in a human liver, and the development of a method of easily measuring fat content in a human organ at low cost.

It is generally known that a fatty liver is closely related to fat content in the liver parenchyma. Although various methods of quantitatively assessing fat content in a target organ have been suggested and carried out, there is a growing need for a method of more easily measuring fat content in a target organ of a human body at a lower cost.

For example, computed tomography (CT) is often used to obtain a cross-sectional image of a human organ, and CT is advantageous in that CT can obtain a high-resolution image and can precisely separate fat from other components in the image without being affected by photographing techniques and conditions. Nevertheless, CT is expensive and dangerous due to radiation exposure.

Also, a biopsy is used to measure fat content in a human organ. The biopsy is a method in which a tissue of an organ, for example, a liver (i.e., a liver biopsy), is removed to analyze the tissue and components of the organ. The liver biopsy can provide very fundamental and reliable results on all kinds of diagnoses and examinations of liver diseases. However, the liver biopsy is complex and invasive to the human body. In addition, the liver biopsy is performed only after there is a sign of disease, and thus, the liver biopsy is not a preventive technique.

Also, ultrasonography is a conventional diagnostic technique based on the cross-sectional image of an organ, e.g., a belly, and ultrasonography is relatively inexpensive and simple to use. In particular, the ultrasonography is safe in that it does not use radioactive rays and is not invasive to the human body. Despite these advantages, the quality of an ultrasonographic image is dependent greatly upon photographing conditions and techniques, and the reflective characteristics and resolution of an object through which ultrasonic waves pass are irregular. For these reasons, there is a high probability that a person diagnosing a disease of a patient may make an arbitrary interpretation on a visual image obtained by ultrasonography, thereby lowering the reliability of the diagnosis of the person.

At present, the clinical determination of a fatty liver using ultrasonography is largely divided into four levels: normal, mild, moderate, and severe. However, an error committed by therapists who are experienced in diagnosing diseases of patients using ultrasonography is by one level or more, and the probability of the occurrence of an error is 20% at maximum. Accordingly, there is a strong demand for a simple and inexpensive method of quantitatively measuring fat content in a target organ using ultrasonography while not being affected by photographing conditions and so on.

In response to such a strong demand, many attempts have been made to measure fat content in a human organ only using ultrasonography. However, it is difficult to quantitatively measure fat content in an organ due to the distortion of image characteristics caused by irregularities in the characteristics of ultrasonograph and photographing conditions.

SUMMARY OF THE INVENTION

The present invention provides a phantom for comparing an image measured by ultrasonograph with a reference image, standardizing the characteristics of the ultrasonograph, and quantitatively measuring fat content as a gray level distribution of an image under photographing conditions readjusted by the phantom, and an apparatus for assessing the accuracy of the ultrasonograph using the phantom.

According to an aspect of the present invention, there is provided a phantom for standardizing ultrasonograph, the phantom comprising: a phantom part including a strong ultrasonic echo material and a weak ultrasonic echo material, which create a gray level distribution in ultrasonography, in a specific composition and ratio, and assessing the accuracy of the ultrasonograph by comparing the composition and ratio of the materials with a composition and ratio of a gray level in an ultrasonographic image; and an outer part surrounding the phantom part.

According to another aspect of the present invention, there is provided a method of obtaining an ultrasonographic image under standardized photographing conditions according to ultrasonograph, the method comprising: obtaining ultrasonographic image using the ultrasonograph in respect to a phantom including a strong ultrasonic echo material and a weak ultrasonic echo material, which create a gray level distribution in ultrasonography, in a specific composition and ratio; comparing in terms of gray level and brightness the obtained ultrasonographic image with a reference image on which the specific composition and ratio of the materials in the phantom are reflected; readjusting at least one of photographing conditions and photographing characteristics of the ultrasonograph based on a difference obtained by the comparison; and obtaining an ultrasonographic image of a target object to be measured using the ultrasonograph of which photographing characteristics are readjusted.

According to another aspect of the present invention, there is provided an apparatus for obtaining an ultrasonographic image under standardized photographing conditions according to ultrasonograph, the apparatus comprising: a phantom photographing unit obtaining an ultrasonographic image using the ultrasonograph in respect to a phantom including a strong ultrasonic echo material and a weak ultrasonic echo material, which create a gray level distribution in ultrasonography, in a specific composition and ratio; an image comparing unit comparing in terms of gray level or brightness the obtained ultrasonographic image with a reference image on which the specific composition and ratio of the materials in the phantom part are reflected; a photographing condition readjusting unit readjusting at least one of photographing conditions and photographing characteristics of the ultrasonograph based on a difference obtained by the comparison of the image comparing unit; and a target image obtaining unit obtaining an ultrasonographic image of a target object to be measured using the ultrasonograph of which photographing characteristics are readjusted.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
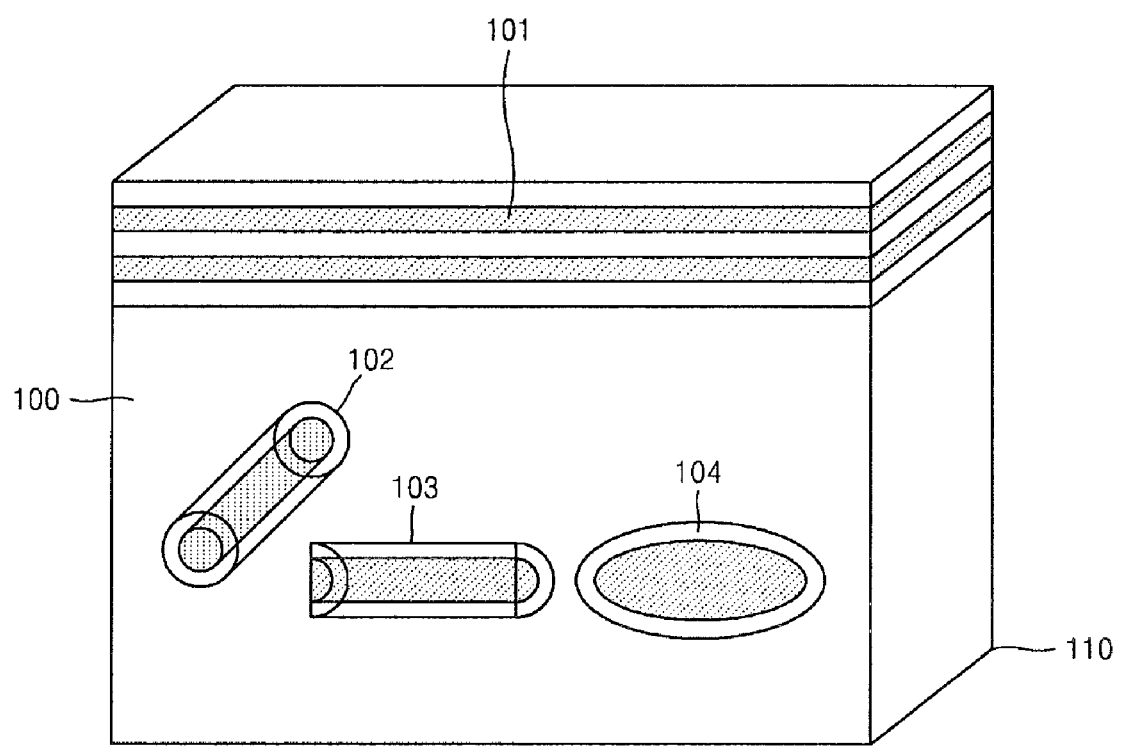
FIG. 1 is a perspective view of a phantom for standardizing ultrasonograph according to an embodiment of the present invention.

FIG. 1 is a perspective view of a phantom for standardizing ultrasonograph (or ultrasonographic equipment) according to an embodiment of the present invention.

FIG. 1 illustrates the phantom for quantitatively measuring fat content in a target organ from an ultrasonographic image. The phantom includes an outer container, and inner structures, installed in the outer container, used to measure a gray level distribution in an ultrasonographic image. Accordingly, the phantom, which can measure the gray level distribution in the ultrasonographic image, can evaluate fat content in the target organ using the ultrasonographic image and can assess the accuracy of ultrasonograph.

The phantom is prepared by inserting structures for simulating a target organ in the belly and a comparative organ, inserting a separate layer, and sealing them. Next, a cross-sectional image of the prepared phantom is photographed, thereby finally determining fat content of the target organ.

Referring to FIG. 1, the phantom includes a phantom part 100 including a strong ultrasonic echo material and a weak ultrasonic echo material, which create a gray level distribution in ultrasonography, in a specific composition and ratio, and assessing the accuracy of ultrasonograph by comparing the specific composition and ratio of the materials with the composition and ratio of a gray level distribution in an image obtained through ultrasonographic imaging, and an outer part 110 surrounding the phantom part 100. In terms of ultrasonic properties, the strong ultrasonic echo material is formed of a fat-equivalent material, and the weak ultrasonic echo material is formed of a water-equivalent material. The ultrasonic properties include an ultrasonic gray level at a specific depth, an ultrasonic attenuation, and a sound speed.

The phantom part 100 includes a skin and fat-equivalent material and a material for fixing inner structures in a container. In detail, the phantom part 100 includes a layered structure 101 including one or more layers, one or more inner structures 102, 103, and 104 disposed under the layered structure 101 and having predetermined volumes, and a fixing structure fixing the inner structures 102, 103, and 104.

The phantom part 100 is a combination of a plurality of structures having different ultrasonic gray levels. The layered structure 101 of the phantom part 100 is formed by alternating a strong ultrasonic echo layer and a weak ultrasonic echo layer. In terms of ultrasonic properties, the strong ultrasonic echo layer is formed of a fat-equivalent material and the weak ultrasonic echo layer is formed of a water-equivalent material.

Each of the inner structures 102, 103, and 104 of the phantom part 100 includes a strong ultrasonic echo material and a weak ultrasonic echo material in a plane perpendicular to the layered structure 101.

For example, the cross-section of each of the inner structures 102 and 104 may include an elliptical weak ultrasonic echo material part and an outer strong echo material part surrounding the elliptical weak ultrasonic echo material part, or include a circular weak ultrasonic echo material part and an outer strong ultrasonic echo material part surrounding the circular weak ultrasonic echo material part.

The cross-section of the inner structure 103 may include a rectangular weak ultrasonic echo material part and an outer strong ultrasonic echo material part contacting the rectangular weak ultrasonic echo material part on opposite two surfaces.

The inner structure 104 has a shape including an ellipsoidal weak ultrasonic echo material part and an outer strong ultrasonic echo material part surrounding the ellipsoidal weak ultrasonic echo material part. Alternatively, each of the inner structures 102 and 103 has a shape including a cylindrical weak ultrasonic echo material part and an outer strong ultrasonic echo material part surrounding a side surface of the cylindrical weak ultrasonic echo material part.

The fixing structure for fixing the inner structures 102, 103, and 104 has an echo characteristic between the echo characteristics of the strong and weak echo characteristic parts of each of the inner structures 102, 103, and 104. The echo characteristic changes in four levels from weak to strong. The fixing structure for fixing the inner structures 102, 103, and 104 is perpendicular to the layered structure 101, is uniform in a plane including all the cross-sections of the inner structures 102, 103, and 104, and has the echo characteristic changing in four levels from weak to strong in a direction perpendicular to the plane.

The ultrasonograph used to photograph the phantom is brightness-modulation (B-mode) ultrasonograph.

Figure 2:
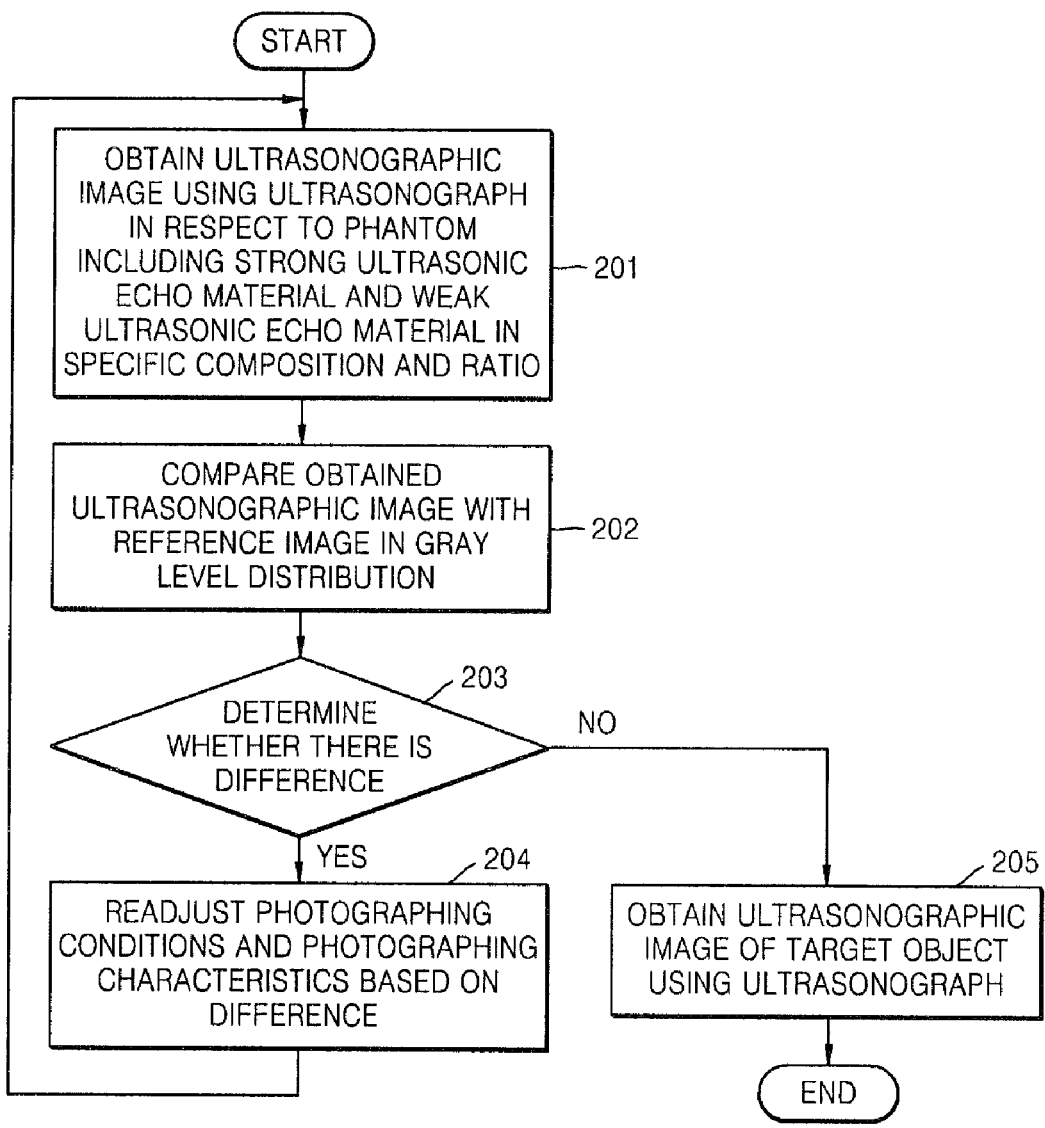
FIG. 2 is a flowchart of a method of obtaining a standardized ultrasonographic image using a phantom for standardizing ultrasonograph, according to an embodiment of the present invention.

FIG. 2 is a flowchart of a method of obtaining a standardized ultrasonographic image using a phantom for standardizing ultrasonograph, according to an embodiment of the present invention.

Referring to FIG. 2, in operation 201, an ultrasonographic image is obtained using ultrasonograph in respect to a phantom including a strong ultrasonic echo material and a weak ultrasonic echo material, which create a gray level distribution in ultrasonography, in a specific composition and ratio. In operation 202, the obtained ultrasonographic image is compared in terms of gray level and brightness with a reference image on which the specific composition and ratio of the materials in the phantom are reflected. In operation 203, it is determined whether there is a difference between the obtained ultrasonographic image and the reference image. If it is determined in operation 203 that there is a difference, the process goes to operation 204. In operation 204, photographing conditions and/or photographing characteristics of the ultrasonograph are readjusted based on the difference between the obtained ultrasonographic image and the reference image. However, if it is determined in operation 203 that there is no difference between the obtained ultrasonographic image and the reference image, the process goes to operation 205. In operation 205, an ultrasonographic image of a target object to be actually measured is obtained using the ultrasonograph of which characteristics are readjusted and standardized. The reference image refers to an ultrasonographic image on which the specific composition and ratio of the materials in the phantom are directly reflected as the gray level distribution under perfect photographing conditions. Also, the reference image is an image on which the materials in the phantom part are accurately reflected within a minimum error range and which can be produced and provided at the same time when the phantom for the ultrasonographic image is prepared.

Figure 3:
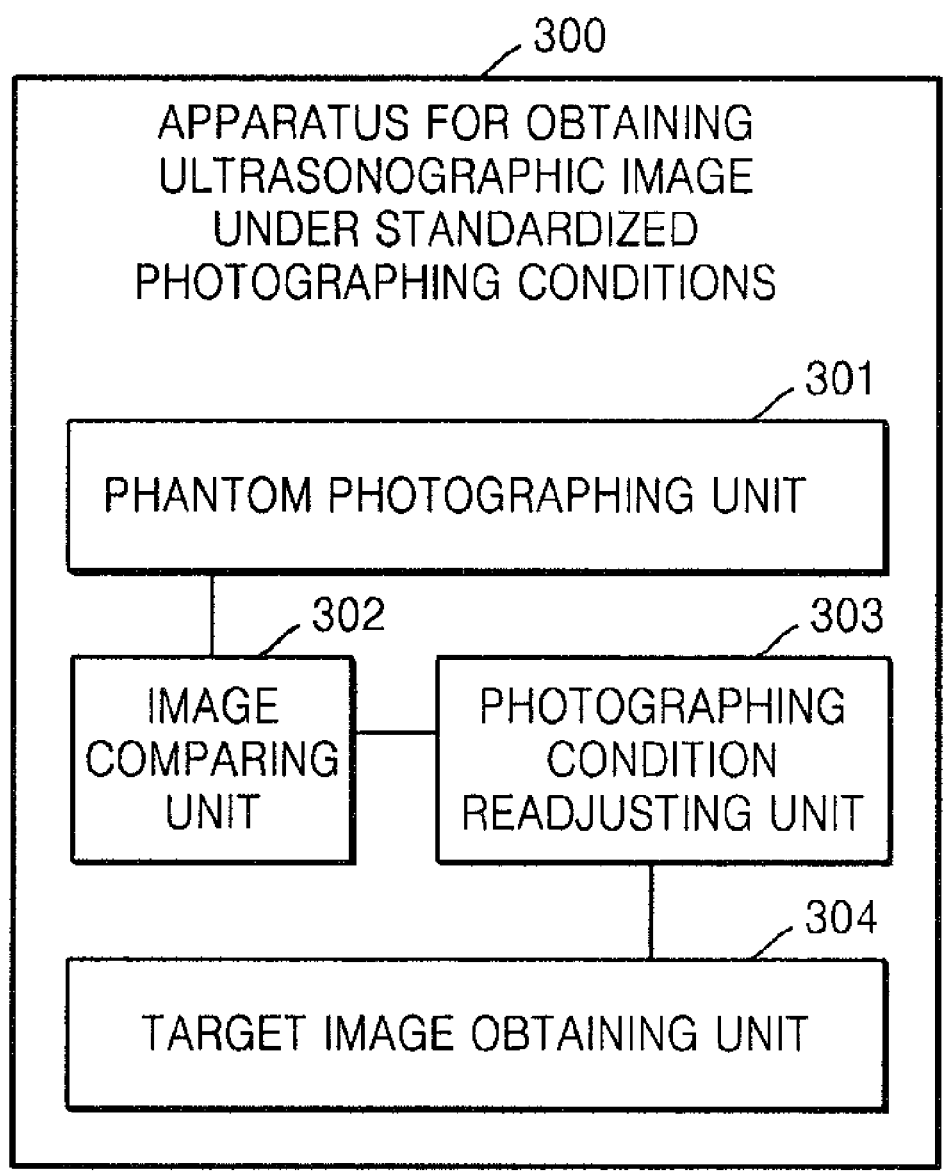
FIG. 3 is a block diagram of an apparatus for obtaining a standardized ultrasonographic image using a phantom for standardizing ultrasonograph, according to an embodiment of the present invention.

FIG. 3 is a block diagram of an apparatus 300 for obtaining a standardized ultrasonographic image using a phantom for standardizing ultrasonograph, according to an embodiment of the present invention.

The apparatus 300 uses a phantom including a fat-equivalent material and a water-equivalent material in terms of ultrasonic properties and an outer container for fixing inner structures, and can standardize the photographing characteristics of ultrasonograph to quantitatively measure fat content in a target organ from an ultrasonographic image. The ultrasonic properties include an ultrasonic gray level at a specific depth, an ultrasonic attenuation, and a sound speed.

Referring to FIG. 3, the apparatus 300 for obtaining an ultrasonographic image under standardized photographing conditions includes a phantom photographing unit 301 obtaining an ultrasonographic image, using the ultrasonograph in respect to the phantom including a strong ultrasonic echo material and a weak ultrasonic echo material, which create a gray level distribution in ultrasonography, in a specific composition and ratio, an image comparing unit 302 comparing the obtained ultrasonographic image in terms of gray level and brightness with a reference image on which the specific composition and ratio of the materials in the phantom are reflected, a photographing condition readjusting unit 303 readjusting photographing conditions and/or photographing characteristics of the ultrasonograph based on a difference obtained by the comparison of the image comparing unit 302, and a target image obtaining unit 304 obtaining an ultrasonographic image of a target object to be actually measured using the ultrasonograph of which characteristics are readjusted. The reference image refers to an ultrasonographic image on which the specific composition and ratio of the materials in the phantom are directly reflected as the gray level distribution under perfect photographing conditions.

The apparatus 300, for obtaining the ultrasonographic image under the standardized photographing conditions, may be used to standardize the photographing characteristics of the ultrasonograph so that a change in reflection and refraction characteristic for an ultrasonic wave of a target organ of a human body which occurs as fat content increases in the target organ can be indexed and fat content can be estimated.

An ultrasonographic image, for example, a cross-sectional image of a belly taken by ultrasonography, is an image obtained by converting the reflective and refractive characteristics of a corresponding organic tissue with regard to ultrasonic waves into a gray level, and then recomposing the gray level into a two-dimensional image. In general, main elements constituting an organic tissue are fat and water. When ultrasonic waves pass through the organic tissue, fat and water have different reflective characteristics from each other. Accordingly, a fat region appears brighter than a water region in an ultrasonographic image. Therefore, the gray level and brightness of a pixel in the cross-sectional image of the belly taken by ultrasonography increases in proportion to fat content in an organic tissue which corresponds to the pixel.

However, the gray level or brightness of a pixel does not represent the fat content in the target organ because the gray level of a pixel may change according to photographing conditions and photographing techniques when the cross-sectional image of the belly is taken by ultrasonography. Therefore, the gray level of a pixel cannot be used as an index of fat content in the organ. For example, when the same position of the same object is taken by ultrasonography two times under different photographing conditions, gray levels for a pixel at the same position may be different in the two images. For this reason, the gray level of the ultrasonographic image cannot be a factor that determines fat content in the organ.

To solve this problem, in the present embodiment, the phantom includes materials that recognize ultrasonographic characteristics and can standardize the photographing characteristics of the ultrasonograph. Accordingly, the apparatus using the phantom can obtain an index of fat content in the target organ without being affected by photographing conditions, thereby obtaining the cross-sectional image of the target organ by ultrasonography.

The present invention may be embodied in a code program, which can be read by a computer, on a computer readable recording medium. The computer readable recording medium includes all kinds of recording apparatuses on which computer readable data are stored. Examples of the computer readable medium include storage media such as magnetic storage media (e.g., read only memories (ROMs), floppy discs, or hard discs), optically readable media (e.g., compact disk-read only memories (CD-ROMs), or digital versatile disks (DVDs) and carrier waves (e.g., transmissions over the Internet). The computer readable recording medium can be dispersively installed in a computer system connected to a network, and stored and executed as a computer readable code in a distributed computing environment. Functional programs, codes, and code segments used for executing the present invention could be easily thought by programmers of skill in the art.

As described above, since the phantom for standardizing the ultrasonograph and the apparatus and method for obtaining the ultrasonographic image using the phantom according to the present invention can readjust the photographing characteristics of the ultrasonograph to obtain a cross-sectional image of a target organ using the ultrasonograph, the ultrasonographic cross-sectional image can be obtained without being affected by the photographing conditions and photographing techniques and standardized fat content in the target organ can be measured. Also, since the fat content in the human organ can be effectively and reliably measured from the ultrasound cross-sectional image, the fat content can be safely measured at low cost.

While the present invention has been particularly shown and described with reference to exemplary embodiments thereof, it will be understood by one of ordinary skill in the art that various changes in form and details may be made therein without departing from the spirit and scope of the present invention as defined by the following claims.

What is claimed is:

1. A phantom for standardizing ultrasonograph, the phantom comprising:
   a phantom part including a strong ultrasonic echo material and a weak ultrasonic echo material, which create a gray level distribution in ultrasonography, in a specific composition and ratio, and assessing the accuracy of the ultrasonograph by comparing the composition and ratio of the materials with a composition and ratio of a gray level in an ultrasonographic image; and
   an outer part surrounding the phantom part,
   wherein the phantom part comprises:
   a layered structure including one or more layers;
   one or more inner structures disposed under the layered structure and having predetermined volumes; and
   a fixing structure fixing the inner structures.

2. The phantom of claim 1, wherein the ultrasonograph is brightness-modulation (B-mode) ultrasonograph.

3. The phantom of claim 1, wherein, in terms of ultrasonic properties, the strong ultrasonic echo material is formed of a fat-equivalent material, and the weak ultrasonic echo material is formed of a water-equivalent material.

4. The phantom of claim 3, wherein the ultrasonic properties include at least one of an ultrasonic gray level at a specific depth, an ultrasonic attenuation, and a sound speed.

5. The phantom of claim 1, wherein the layered structure is formed by alternating a strong ultrasonic echo material layer and a weak ultrasonic echo material.

6. The phantom of claim 1, wherein each of the inner structures includes a strong ultrasonic echo material part and a weak ultrasonic echo material part disposed in a plane perpendicular to the layered structure.

7. The phantom of claim 6, wherein the cross-section of each of the inner structures includes an elliptical or circular weak ultrasonic echo material part and an outer strong ultrasonic echo material part surrounding the elliptical or circular weak ultrasonic echo material part.

8. The phantom of claim 6, wherein the cross-section of each of the inner structures includes a rectangular weak ultrasonic echo material part and a strong ultrasonic echo material part contacting the rectangular weak ultrasonic echo material part.

9. The phantom of claim 6, wherein each of the inner structures has a shape including an inner ellipsoidal or cylindrical weak ultrasonic echo material part and an outer strong ultrasonic echo material part surrounding the inner ellipsoidal or cylindrical weak ultrasonic echo material part.

10. The phantom of claim 1, wherein the fixing structure is formed of a material with an echo characteristic between the echo characteristics of the strong and weak ultrasonic echo material parts of each of the inner structures.

11. The phantom of claim 10, wherein the echo characteristic of the fixing structure changes in four levels from weak to strong.

12. The phantom of claim 11, wherein the fixing structure is perpendicular to the layered structure, is uniform in a plane including the cross-sections of the inner structures, and has the echo characteristic changing in a direction perpendicular to the plane.

13. A method of obtaining an ultrasonographic image under standardized photographing conditions according to ultrasonograph, the method comprising:
   obtaining ultrasonographic image using the ultrasonograph in respect to a phantom including a strong ultrasonic echo material and a weak ultrasonic echo material, which create a gray level distribution in ultrasonography, in a specific composition and ratio;
   comparing in terms of gray level and brightness the obtained ultrasonographic image with a reference image on which the specific composition and ratio of the materials in the phantom are reflected;
   readjusting at least one of photographing conditions and photographing characteristics of the ultrasonograph based on a difference obtained by the comparison; and
   obtaining an ultrasonographic image of a target object to be measured using the ultrasonograph of which photographing characteristics are readjusted,
   wherein the phantom comprises:
   a layered structure including one or more layers;
   one or more inner structures disposed under the layered structure and having predetermined volumes; and
   a fixing structure fixing the inner structures.

14. The method of claim 13, wherein the reference image is an ultrasonographic image on which the specific composition and ratio of the materials in the phantom part are directly reflected as the gray level distribution under perfect photographing conditions.

15. The method of claim 13, wherein the ultrasonograph is brightness-modulation (B-mode) ultrasonograph.

16. The method of claim 13, wherein, in terms of ultrasonic properties, the strong ultrasonic echo material is formed of a fat-equivalent material and the weak ultrasonic echo material is formed of a water-equivalent material.

17. An apparatus for obtaining an ultrasonographic image under standardized photographing conditions according to ultrasonograph, the apparatus comprising:
   a phantom photographing unit obtaining an ultrasonographic image using the ultrasonograph in respect to a phantom including a strong ultrasonic echo material and a weak ultrasonic echo material, which create a gray level distribution in ultrasonography, in a specific composition and ratio;
   an image comparing unit comparing in terms of gray level or brightness the obtained ultrasonographic image with a reference image on which the specific composition and ratio of the materials in the phantom part are reflected;

a photographing condition readjusting unit readjusting at least one of photographing conditions and photographing characteristics of the ultrasonograph based on a difference obtained by the comparison of the image comparing unit; and a target image obtaining unit obtaining an ultrasonographic image of a target object to be measured using the ultrasonograph of which photographing characteristics are readjusted, wherein the phantom comprises:

a layered structure including one or more layers;

one or more inner structures disposed under the layered structure and having predetermined volumes; and a fixing structure fixing the inner structures.

18. The apparatus of claim 17, wherein the reference image is an ultrasonographic image on which the specific composition and ratio of the materials in the phantom are directly reflected as the gray level distribution under perfect photographing conditions.

19. The apparatus of claim 18, wherein, in terms of ultrasonic properties, the strong ultrasonic echo material is formed of a fat-equivalent material and the weak ultrasonic echo material is formed of a water-equivalent material.

* * * * *